United States Patent [19]

Tamura et al.

[11] Patent Number: 5,104,414
[45] Date of Patent: Apr. 14, 1992

[54] 2-ALKYL-4-METHOXY-5-AMINOPHENOL OR SALT THEREOF, OR 2-ALKYL-4-METHOXY-5-SUBSTITUTED AMINOPHENOL OR SALT THEREOF, AND DYEING COMPOSITION FOR KERATIN FIBERS COMPRISING THE SAME

[75] Inventors: Tadashi Tamura; Akira Kiyomine; Yoshinori Nishizawa, all of Tochigi; Hidetoshi Tagami, Tokyo; Toru Yoshihara, Tokyo; Jiro Kawase, Tokyo, all of Japan

[73] Assignee: Kao Corporation, Tokyo, Japan

[21] Appl. No.: 694,154

[22] Filed: May 1, 1991

Related U.S. Application Data

[63] Continuation-in-part of Ser. No. 558,538, Jul. 27, 1990.

[30] Foreign Application Priority Data

Jul. 28, 1989 [JP] Japan ................... 1-195611
Jul. 28, 1989 [JP] Japan ................... 1-195612
Sep. 1, 1989 [JP] Japan ................... 1-227249
Jul. 27, 1990 [JP] Japan ................... 2-200958

[51] Int. Cl.$^5$ ................................. A61K 7/13
[52] U.S. Cl. ........................... 8/408; 8/412; 8/421; 8/424; 564/443; 568/706
[58] Field of Search ................. 8/408, 412, 421, 424; 564/443; 568/706

[56] References Cited

PUBLICATIONS

Sensh and Sakan, "Synthesis of DL-3,6-Dihydroxykynurenine" Chem. Abstracts, 52–7157e; 1958 (4–Nitro-3,-5-Dimethoxybenzoic acid).

Primary Examiner—A. Lionel Clingman
Assistant Examiner—William S. Parks
Attorney, Agent, or Firm—Sughrue, Mion, Zinn, Macpeak & Seas

[57] ABSTRACT

A 2-alkyl-4-methoxy-5-aminophenol or a salt thereof; a 2-alkyl-4-methoxy-5-nitrophenol or 2-alkyl-4-methoxy-5-nitrophenyl mesylate, each an intermediate in the preparation of the 2-alkyl-4-methoxy-5-aminophenol; and a dyeing composition for keratin fibers comprising a color-developing material and the 2-alkyl-4-methoxy-5-aminophenol or the salt thereof as a coupling agent are disclosed.

Further, a 2-alkyl-4-methoxy-5-substituted aminophenol or a salt thereof; a 2-alkyl-4-methoxy-5-substituted aminophenol derivative, which is an intermediate in the preparation of the 2-alkyl-4-methoxy-5-substituted aminophenol; and a dyeing composition for keratin fibers comprising a color-developing material and the 2-alkyl-4-methoxy-5-substituted aminophenol, the salt thereof, or the 2-alkyl-4-methoxy-5-substituted aminophenol derivative as a coupling agent are disclosed.

3 Claims, No Drawings

2-ALKYL-4-METHOXY-5-AMINOPHENOL OR SALT THEREOF, OR 2-ALKYL-4-METHOXY-5-SUBSTITUTED AMINOPHENOL OR SALT THEREOF, AND DYEING COMPOSITION FOR KERATIN FIBERS COMPRISING THE SAME

This is a continuation-in-part of application Ser. No. 07/558,538 filed July 27, 1990.

FIELD OF THE INVENTION

This invention relates to a novel 2-alkyl-4-methoxy-5-aminophenol or a salt thereof, a dyeing composition for keratin fibers comprising the same, and a novel derivative thereof, which is an intermediate in the preparation of the 2-alkyl-4-methoxy-5-aminophenol.

The present invention further relates to a novel 2-alkyl-4-methoxy-5-substituted aminophenol, a novel derivative thereof, which is an intermediate in the preparation of the 2-alkyl-4-methoxy-5-substituted aminophenol, and a dyeing composition for keratin fibers comprising these compounds.

BACKGROUND OF THE INVENTION

So-called oxidation dyes, wherein a color-developing material is combined with a coupling agent, have been widely used in dyeing keratin fibers such as the hair. In the case of such an oxidation dye, a so-called oxidation pigment, which has been formed by the oxidation coupling of a color-developing material with a coupling agent, would intensely dye, for example, the hair.

Known examples of the color-developing material include p-phenylenediamine derivatives, p-aminophenol derivatives, diaminopyridine derivatives, 4-aminopyrazolone derivatives and heterocyclic hydrazone derivatives; while known examples of the coupling agent include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, hydroquinone, 2,4-diaminoanisole, m-toluylenediamine, 4-aminophenol, resorcin, resorcin monomethyl ether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxyquinolone-2,1-amino-3-acetylacetamino-4-nitrobenzene, 1-amino-3-cyanoacetylamino-4-nitro-benzene, m-aminophenol, 4-chlororesorcin, 2-methylresorcin, 2,4-diaminophenoxyethanol, 2,6-diaminopyridine, 3,5-diamino-trifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine, p-nitro-o-phenylenediamine, 2-amino-5-nitrophenol, p-nitro-m-phenylenediamine, o-nitro-p-phenylenediamine and 2-amino-4-nitrophenol.

However known oxidation dyes are unsatisfactory in chroma, dyeability power and fastness. Since these properties largely depend on the properties of the employed coupling agents, it is highly important in the preparation of an excellent oxidation dye to find out a material which is excellent as a coupling agent.

SUMMARY OF THE INVENTION

Under these circumstances, we have synthesized a number of compounds and examined their properties as a coupling agent. As a result, we have found out that a 2-alkyl-4-methoxy-5-aminophenol represented by formula (I) below or a salt thereof, or a 2-alkyl-4-methoxy-5-substituted aminophenol represented by formula (III) below or a salt thereof is excellent from the viewpoint of the above-mentioned properties, thus completing the present invention.

Accordingly, the present invention provides a 2-alkyl-4-methoxy-5-aminophenol represented by formula (I) below or a salt thereof:

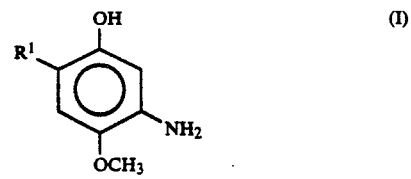

wherein $R^1$ represents a substituted or unsubstituted lower alkyl group; and
a 2-alkyl-4-methoxy-5-nitrophenyl mesylate or 2-alkyl-4-methoxy-5-nitrophenol represented by formula (II) below, each an intermediate in the preparation of the compound of formula (I) above:

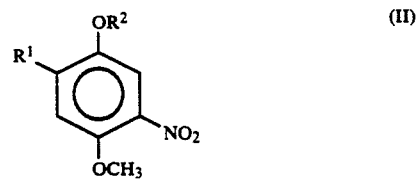

wherein $R^1$ represents a substituted or unsubstituted lower alkyl group; and $R^2$ represents a hydrogen atom or a mesyl group.

The present invention further provides a dyeing composition for keratin fibers comprising the compound represented by formula (I) as a coupling agent.

The present invention furthermore provides a 2-alkyl-4-methoxy-5-substituted aminophenol represented by formula (III) below or a salt thereof:

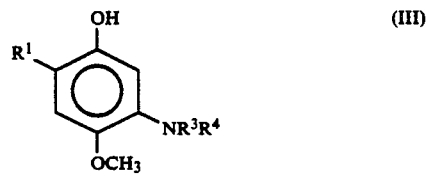

wherein $R^1$ represents a substituted or unsubstituted lower alkyl group; $R^3$ represents a hydrogen atom, a substituted or unsubstituted lower alkyl group or a substituted or unsubstituted hydroxyalkyl group; and $R^4$ represents a substituted or unsubstituted lower alkyl group, a substituted or unsubstituted mono- or di-hydroxyalkyl group, a substituted or unsubstituted lower alkanoyl group, a substituted or unsubstituted arylcarbonyl group, or a substituted or unsubstituted lower alkylsulfonyl group.

The present invention still provides a novel 2-alkyl-4-methoxy-5-substituted aminophenol derivative represented by formula (IV) or (V):

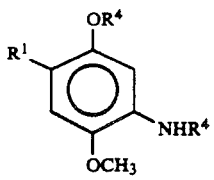

wherein R¹ represents a substituted or unsubstituted lower alkyl group; and R⁴ and R⁴', which may be the same or different, each represents a substituted or unsubstituted lower alkyl group, a substituted or unsubstituted mono- or di-hydroxyalkyl group, a substituted or unsubstituted lower alkanoyl group, a substituted or unsubstituted arylcarbonyl group, or a substituted or unsubstituted lower alkylsulfonyl group;

and

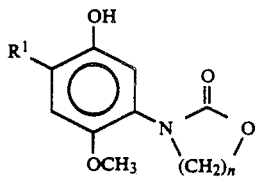

wherein R¹ represents a substituted or unsubstituted lower alkyl group and n is an integer of 2 to 4.

The present invention still further provides a dyeing composition for keratin fibers comprising the compound represented by formula (III) as a coupling agent.

The present invention still furthermore provides a dyeing composition for keratin fibers comprising the compound represented by formula (IV) as a coupling agent.

DETAILED DESCRIPTION OF THE INVENTION

The definitions for R¹, R², R³, R⁴ and R⁴' in formulae from (I) through (V) above are explained below in more detail.

Examples of the substituted or unsubstituted lower alkyl group include the alkyl groups having 1 to 5 carbon atoms, preferably 1 to 3 carbon atoms, and the examples of the substituent which may substitute therefore include alkyl group, hydroxyalkyl group, the group of $\text{-(CH}_2)_m\text{-O-(CH}_2)_m\text{-OH}$ wherein m is an integer of 1 to 5, and the like. Specific Examples the substituted or unsubstituted lower alkyl group include methyl, ethyl, propyl, iso-propyl, n-butyl, sec-butyl and amyl groups. Among them, methyl, and ethyl are preferred.

Examples of the substituted or unsubstituted mono-or di-hydroxyalkyl group include those in which an alkyl moiety thereof contain 2 to 10 carbon atoms, preferably 2 to 3 carbon atoms and contain 1 to 3, preferably 1 to 2 hydroxy group(s), and the examples of the substituent which may substitute therefor include methyl, ethyl, propyl, and the like. The hydroxy group(s) is preferably contained in the hydroxyalkyl group at β- or γ-position. Specific examples of the substituted or unsubstituted hydroxyalkyl group include 2-hydroxyethyl, 2-hydroxypropyl, 2,3-dihydroxypropyl and 3-hydroxypropyl.

Among them, 2-hydroxyethyl and 2-hydroxypropyl are preferred.

Examples of the substituted or unsubstituted lower alkanoyl group include substituted or unsubstituted straight-chain or branched alkanoyl group having 1 to 5 carbon atoms. Examples of the substituent which may substitute for the lower alkanoyl group include a halogen atom such as fluorine atom, chlorine atom, and bromine atom. The lower alkanoyl group may be substituted by one or two or more of these halogen atoms. Specific examples of the substituted or unsubstituted acetyl group include formyl, acetyl, fluoroacetyl, difluoroacetyl, trifluoroacetyl, chloroacetyl, dichloroacetyl, trichloroacetyl, propyonyl, butylyl, valeryl and isovaleryl groups. Among them, acetyl, fluoroacetyl, difluoroacetyl and trifluoroacetyl are preferred.

Examples of the substituted or unsubstituted arylcarbonyl group include those having 7 to 15 carbon atoms, preferably 7 to 10 carbon atoms, and examples of the substituent therefor include methyl, t-butyl, nitro and chlorine. Specific examples thereof include benzoyl, toluoyl, m-nitrobenzoyl, chlorobenzoyl and naphthoyl groups. Among them, benzoyl and toluoyl are preferred.

Examples of the substituted or unsubstituted lower alkylsulfonyl group include methanesulfonyl and ethanesulfonyl groups.

Specific examples of the 2-alkyl-4-methoxy-5-aminophenol compound represented by formula (I), the 2-alkyl-4-methoxy-5-substituted aminophenol compound represented by formula (III) and the 2-alkyl-4-methoxy-5-substituted aminophenol derivative represented by formula (IV), each according to the present invention, will be mentioned below. However, the present invention is not construed to be restricted thereby.

Examples of the 2-alkyl-4-methoxy-5-aminophenol compound represented by formula (I) include 2-methyl-4-methoxy-5-aminophenol 2-ethyl-4-methoxy-5-aminophenol, 2-propyl-4-methoxy-5-aminophenol and 2-t-butyl-4-methoxy-5-aminophenol.

Examples of 2-alkyl-4-methoxy-5-substituted aminophenol compound represented by formula (III) include 2-methyl-4-methoxy-5-methylaminophenol, 2-methyl-4-methoxy-5-ethylaminophenol, 2-methyl-4-methoxy-5-mesylaminophenol, 2-methyl-4-methoxy-5-dimethylaminophenol, 2-methyl-4-methoxy-5-diethylaminophenol, 2-methyl-4-methoxy-5-benzoylaminophenol, 2-methyl-4-methoxy-5-acetylaminophenol, 2-methyl-4-methoxy-5-(fluoroacetyl)aminophenol, 2-methyl-4-methoxy-5-(difluoroacetyl)aminophenol, 2-methyl-4-methoxy-5-(trifluoroacetyl)-aminophenol, 2-methyl-4-methoxy-5-(2-hydroxyethyl)aminophenol, 2-methyl-4-methoxy-5-(2-hydroxypropyl)aminophenol, and 2-methyl-4-methoxy-5-bis(2-hydroxypropyl)aminophenol.

Examples of the 2-alkyl-4-methoxy-5-substituted aminophenol derivative represented by formula (IV) include 2-methyl-4-methoxy-5-aminophenyl acetate.

The 2-alkyl-4-methoxy-5-aminophenol of the formula (I) of the present invention may be prepared by, for example, methylating a 2-alkyl-4-hydroxy-5-nitrophenyl mesylate of formula (VI) to thereby give a compound of formula (IIa), demesylating the compound of formula (IIa) to thereby give a compound of (VII) and then reducing the compound of formula (VII), in accordance with the following reaction scheme:

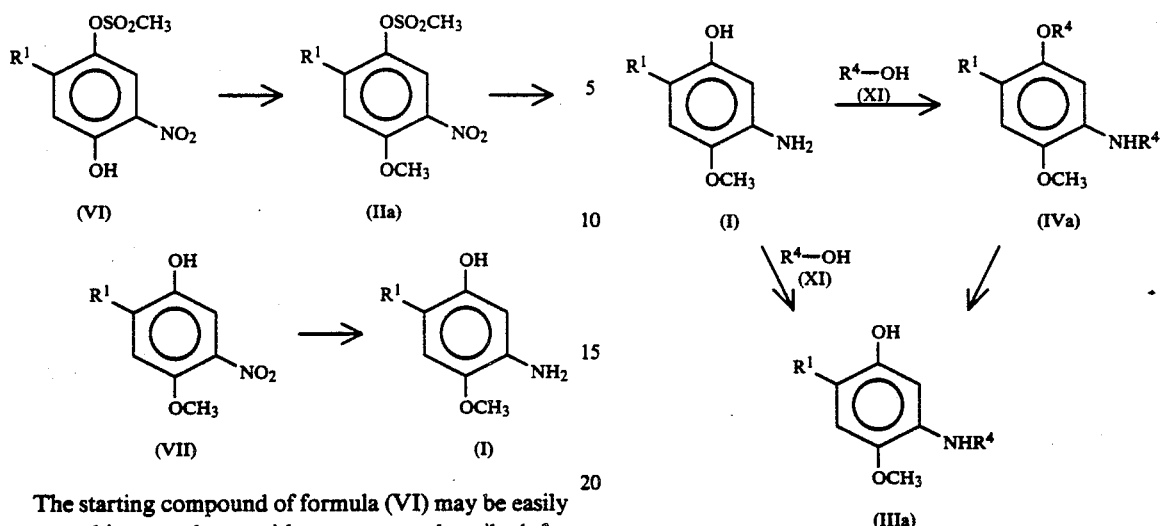

The starting compound of formula (VI) may be easily prepared in accordance with a manner as described, for example, in Japan Kokai 62-240960.

The starting compound of formula (VI) may be methylated by common methods for methylating phenols. Among these methods, the dimethyl sulfate method is convenient and effective. The demesylation of the compound (IIa) may be preferably conducted in an alkali. The compound (VII) may be reduced by a common method for reducing a nitro group. Catalytic hydrogenation or reduction with an aqueous solution of acetic acid/iron is convenient and effective. In the catalytic hydrogenation, palladium, platinum, copper or nickel may be used as a catalyst. As a solvent therefor, methanol, ethanol, ethyl acetate or dimethylformamide may be selected. The reaction may be conducted at a temperature ranging from room temperature to the boiling point of the solvent selected. The hydrogen gas pressure may range from 1 to 250 kg/cm². After the completion of the reduction, the catalyst is removed by filtration. After concentration, the filtrate may be easily purified by distillation or recrystallization. The reduction with an aqueous solution of acetic acid/iron may be conducted by adding a solvent miscible with the aqueous solution of acetic acid, for example, methanol, ethanol, acetone, N,N-dimethylformamide, if required, and heating the obtained mixture under reflux in the presence of excessive iron. After the completion of the reaction, the solid matters are filtered off. After extracting with an appropriate organic solvent, the filtrate may be easily purified by distillation or recrystallization.

The 2-alkyl-4-methoxy-5-substituted aminophenol of formula (III) and the 2-alkyl-4-methoxy-5-substituted aminophenol derivative of formula (IV) of the present invention may be prepared by, for example, introducing substituent(s) to the amino group of the compound represented by formula (I) above in conventional manners.

For example, the 2-alkyl-4-methoxy-5-substituted aminophenol of formula (IIIa) and the 2-alkyl-4-methoxy-5-substituted aminophenol derivative of formula (IVa) below may be prepared in accordance with the following reaction scheme:

wherein $R^1$ and $R^4$ are defined as above.

That is, the 2-alkyl-4-methoxy-5-substituted aminophenol (IIIa) and the 2-alkyl-4-methoxy-5-substituted aminophenol derivative (IVa) may be prepared by allowing to react a compound of formula (XI) or a derivative thereof with aminophenol of formula (I) to give a compound (IVa) or a compound (IIIa). The compound (IIIa) may also be prepared by hydrolyzing the compound (IVa).

The compound (IVa) may be prepared, for example, by allowing to react a reactive derivative of the compound (XI) such as an acid anhydride and an acid halide with the compound (I) in accordance with a common acylating reaction. Further, the compound (IIIa) may be prepared, for example, by allowing to react a methyl ester of the compound (XI) with the compound (I) in accordance with a common acid amide formation reaction. Also, hydrolysis of the compound (IVa) may preferably be conducted in the presence, for example, of an alkali in accordance with a conventional manner.

Further, for example, the 2-alkyl-4-methoxy-5-substituted aminophenol of formula (IIIb) below may be prepared by acylating a 2-alkyl-4-methoxy-5-aminophenol of formula (I) above with β-chloroethyl chloroformate to give compound (VIII), and then conducting cyclization to give 1,3-oxazolidin-2-one (Va), followed by hydrolysis thereof to obtain 2-alkyl-4-methoxy-5-(2-hydroxyethyl)aminophenol, in accordance with the following reaction scheme.

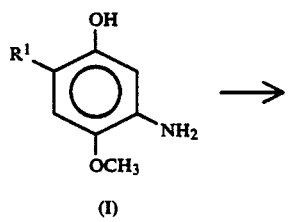

-continued

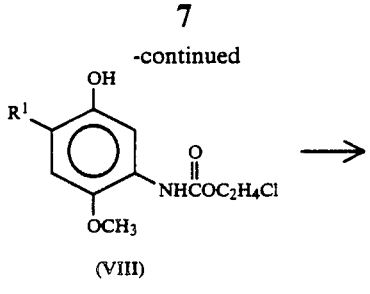
(VIII)

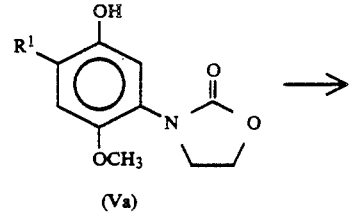
(Va)

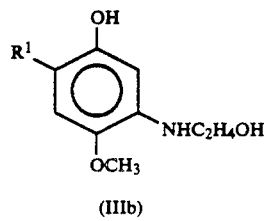
(IIIb)

wherein R¹ is defined as above.

Each of the compound of formula (I) or (III) of the present invention may be converted into a salt of an organic or inorganic acid (for example, hydrochloric acid, sulfuric acid, phosphoric acid, acetic acid, propionic acid, lactic acid, citric acid) to thereby improve the workability during the formulation.

When the compound of formula (I), (III) or (IV) of the present invention is used as a coupling agent together with a known color-development material, a dyeing composition for keratin fibers showing a wide range of color tone (yellow to red to blue) can be obtained.

As the color-developing material to be used in the present invention, those commonly employed in oxidation hair dyes may be selected. Examples thereof include p-phenylenediamine derivatives such as p-phenylenediamine, toluene-2,5-diamine, N-phenyl-p-phenylenediamine and 2-chloro-p-phenylenediamine; p-aminophenol derivatives such as p-aminophenol, 5-aminosalicylic acid and 2,4-diaminophenol; pyridine derivatives such as 2,5-diaminopyridine and 2,3-diaminopyridine; and pyrimidine derivatives such as tetraaminopyrimidine.

Among these color-developing materials, p-aminophenol derivatives represented by formula (IX) below are preferred in combination with the compound of formula (I) or with the compound of formula (III) in which R⁴ is a hydroxyalkyl group:

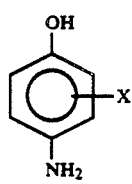
(IX)

wherein X represents hydrogen atom, a halogen atom, carboxyl group or acetylamino group;

to obtain a reddish color tone of an extremely high chroma and a high fastness. Examples of the compound of formula (XI) include p-aminophenol, 5-aminosalicylic acid, 3-carboxyl-4-aminophenol, 2-acetylamino-4-aminophenol and 2-chloro-4-aminophenol.

On the other hand, p-phenylenediamine derivatives represented by formula (X) are preferred in combination with the compound of formula (III) in which R⁴ is the lower alkanoyl group or the lower alkylsulfonyl group or with the compound of formula (IV):

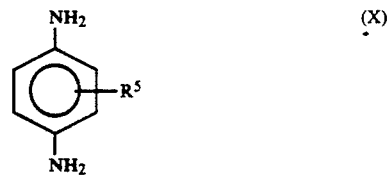
(X)

wherein R⁵ represents a hydrogen atom, a chlorine atom, a methyl group, a hydroxyethyl group or a β-hydroxyethoxy group;

to obtain a bluish color tone of an extremely high chroma and a high fastness.

The dyeing composition of the present invention may comprise other coupling agent(s). In some cases, it is also possible to add a substantive dye to the dyeing composition of the present invention so as to additionally change the color. Examples of such a substantive dye include those specified as *Standard Dyeing Materials* published by Japan Hair Color Association, such as 2-amino-4-nitrophenol, 2-amino-5-nitrophenol, nitro-p-phenylenediamine hydrochloride, nitro-p-phenylenediamine, p-aminophenylsulfamic acid, p-nitro-o-phenylenediamine, picramic acid, sodium picramate, picric acid, chrome brown RH, hematein, nitro-p-phenylenediamine sulfate, p-nitro-o-phenylenediamine sulfate, p-nitro-m-phenylenediamine sulfate, 1-amino-4-methylaminoanthraquinone and 1,4-diaminoanthraquinone; acid dyes such as Red No. 2, Red No. 3, Red No. 102, Red No. 104, Red No. 105, Red No. 106, Yellow No. 4, Yellow No. 5, Green No. 3, Blue No. 1, Blue No. 2, Red No. 201, Red No. 227, Red No. 230, Red No. 231, Red No. 232, Orange No. 205, Orange No. 207, Yellow No. 202, Yellow No. 203, Green No. 201, Green No. 204, Green No. 205, Blue No. 202, Blue No. 203, Blue No. 205, Brown No. 201, Red No. 401, Red No. 502, Red No. 503, Red No. 504, Red No. 506, Orange No. 402, Yellow No. 402, Yellow No. 403, Yellow No. 406, Yellow No. 407, Green No. 401, Green No. 402, Purple No. 401 and Black No. 401; oil-soluble dyes such as Red No. 215, Red No. 218, Red No. 225, Orange No. 201, Orange No. 206, Yellow No. 201, Yellow No. 204, Green No. 202, Purple No. 201, Red No. 501, Red No. 505, Orange No. 403, Yellow No. 404, Yellow No. 405 and Blue No. 403; basic dyes such as Red No. 213 and Red No. 214; and basic dyes manufactured by Arianor Co. such as Sienna Brown, Mahogany, Madder Red, Steel Blue and Straw Yellow. Among these dyes, nitro-phenylenediamine, nitro-aminophenol and anthraquinone are preferable.

The dyeing composition of the present invention may (auto) oxidized coupling with oxygen in the atmosphere so as to dye, for example, the hair. However it is preferable to induce the oxidation coupling by adding a chemical oxidizing agent thereto. Examples of particularly preferable oxidizing agents include hydrogen peroxide; products obtained by adding hydrogen peroxide to urea, melamine or sodium borate; and mixtures of such a hydrogen peroxide adduct with potassium peroxide disulfate.

The dyeing composition of the present invention may be preferably provided in the form of, for example, cream, emulsion, gel, solution. The dyeing composition of the present invention may be formulated into such a form by adding various additives commonly employed in the field of cosmetics (for example, wetting agent (emulsifier), solubilizer, thickener, stabilizer, texture improver, hair styling base, perfume) to the above-mentioned color-developing material and coupling agent and processing the obtained mixture in a conventional manner. Examples of the wetting agent (emulsifier) which can be used in the present invention include alkyl benzenesulfonates, fatty alcohol sulfates, alkyl sulfonates, fatty acid alkanol amides and adducts of ethylene oxide to fatty alcohols. Examples of the thickener include methyl cellulose, starch, higher fatty alcohol, paraffin oil and fatty acids. Examples of the stabilizer include reducing agents such as sulfites, and hydroquinone derivatives and chelating agents. Examples of the texture improver and the hair styling base include silicone, higher alcohols, oils such as various nonionic surfactants and various cationic polymers.

These compositions may contain the color-developing material and the coupling agent in an amount in total of from 0.2 to 10% (by weight based on the total weight of the composition, the same will apply hereinafter), preferably from 1 to 5%. The wetting agent (emulsifier) and the thickener may be usually used respectively in amounts of from 0.5 to 30% and from 0.1 to 25%.

It is preferable that the pH value of the total composition is adjusted to pH of from 8 to 10.

Keratin fibers may be dyed with the dyeing composition of the present invention, for example, in the following manner. First, an oxidizing agent is added to the dyeing composition of the present invention so as to induce oxidation coupling. The dyeing solution thus obtained is applied to the keratin fibers. After allowing to stand for 10 to 50 minutes, preferably 25 to 35 minutes, the keratin fibers are washed and then dried. The application of the dyeing solution may be conducted at from 15° to 40° C.

As described above, the use of the 2-alkyl-4-methoxy-5-substituted aminophenol of the present invention or a salt thereof, or the 2-alkyl-4-methoxy-5-substituted aminophenol or a salt thereof in a dyeing composition for keratin fibers comprising a color-developing material and a coupling agent makes it possible to dye keratin fibers over a wide range of color tone. The color tone thus obtained is excellent in chroma, dyeability power and fastness. When the 2-alkyl-4-methoxy-5-aminophenol of formula (I) or the 2-alkyl-4-methoxy-5-substituted aminophenol of formula (III) in which $R^4$ is a hydroxyalkyl group, is combined with a p-aminophenol derivative which is used as a color-developing material, a reddish color tone of an extremely high chroma and a high fastness can be obtained. Alternatively, when the 2-alkyl-4-methoxy-5-substituted aminophenol of formula (III) in which $R^4$ is the lower alkanoyl group or the lower alkylsulfonyl group or the 2-alkyl-4-methoxy-5-substituted aminophenol derivative of formula (IV) is combined with a p-phenylenediamine derivative which is used as a color-developing material, a bluish color tone of an extremely high chroma and a high fastness can be obtained. Furthermore, the color tone thus obtained is highly resistant against light, washing and rubbing.

To further illustrate the present invention, and not by way of limitation, the following Referential Examples and Examples will be given.

EXAMPLE 1

(i) To 200 ml of acetone, were added 19.1 g (77.3 mmol) of 2-methyl-4-hydroxy-5-nitrophenyl mesylate, 31.2 g of sodium carbonate and 19.2 g of dimethyl sulfate. The obtained mixture was heated under reflux for 3 hours. The reaction mixture was cooled and 700 ml of water was poured thereto. Then the mixture was extracted with 700 ml of chloroform, and the extract was washed with water and dried over anhydrous Glauber's salt. After distilling off the solvent under reduced pressure, the residue was recrystallized from a solvent mixture (hexane/acetone (2:1, by volume)) to thereby give 15.4 g (59.1 mmol) of 2-methyl-4-methoxy-5-nitropheyl mesylate. The yield was 77%.

Physical Properties of
2-methyl-4-methoxy-5-nitropheyl mesylate m.p.: 110.0°–113.0° C.
$^1$H-NMR spectra (200 MHz, CDCl$_3$): δppm; 2.44 (3H,s), 3.25 (3H,s), 3.97 (3H, s), 6.98 (1H, s), 7.87 (1H, s).
IR spectra (KBr): $\nu$cm$^{-1}$; 1524, 1372, 1346, 1172.
Elementary analysis data: caluculated valu for C$_9$H$_{11}$NO$_6$S: C: 41.38%, H: 4.24%, N: 5.36%, S: 12.27%; analyzed value: C: 41.46%, H: 4.38%, N: 5.36%, S: 12.28%.

(ii) In 110 ml of methanol was dissolved 15.5 g (59.4 mmol) of 2-methyl-4-methoxy-5-nitropheyl mesylate. Then 6.5 g of sodium hydroxide dissolved in 20 ml of water was added thereto. The obtained mixture was heated under reflux for 1 hour. After cooling, concentrated hydrochloric acid was added to thereby acidify the mixture. Then 400 ml of water was added and crystals were precipitated. The crystals were collected by filtration and washed with water. Thus 10.9 g (59.4 mmol) of 2-methyl-4-methoxy-5-nitrophenol was obtained. The yield was 100%.

Physical Properties of
2-methyl-4-methoxy-5-nitrophenol m.p.: 79.5°–80.5° C.
$^1$H-NMR spectra (200 MHz, DMSO-d$_6$): δppm; 2.21 (3H, s), 3.83 (3H, s), 7.15 (1H, s), 7.29 (1H, s), 9.74 (1H, s).
IR spectra (KBR): $\nu$cm$^{-1}$; 3526, 1528, 1338.
Elementary analysis data: caluculated value for C$_8$H$_9$NO$_4$: C: 52.46%, H: 4.95%, N: 7,65%; analyzed value: C: 52.55%, H: 5.06%, N: 7.55%.

(iii) 320 mg of 10% palladium-on-carbon, 2.90 g (15.8 mmol) of 2-methyl-4-methoxy-5-nitrophenol and 75 ml of ethanol were fed into an autoclave (300 ml). The mixture was then hydrogenated at 50° C. under 50 kg/cm$^2$ for 5 hours. After allowing to cool, the catalyst was filtered off and the solvent was distilled off under reduced pressure. Thus 19.0 g (12.4 mmol) of 2-methyl-4-methoxy-5-aminophenol was obtained in the form of brown crystals. The $^1$H-NMR spectra of this product showed no impurities. The yield was 78%.

The 2-methyl-4-methoxy-5-aminophenol was purified by silica gel column chromatography (Silica Gel 60, trade name, manufactured by Merck Co., 230–400 mesh, 200 g, eluent: acetone/chloroform (1:1, by volume)) and dissolved in ether. Then a hydrogen chloride gas was blown thereto to thereby give 2-methyl-4-methoxy-5-aminophenol hydrochloride.

Physical Properties of 2-methyl-4-methoxy-5-aminophenol hydrochloride m.p.: 197°–203° C. (decomposed).

1H-NMR (200 MHz, DMSO-$d_6$): δppm: 2.12 (3H, s), 3.78 (3H,s), 6.96 (1H, s), 7.02 (1H, s), 9.05 (1H, br), 9.99 (3H, br).

IR spectra: $v cm^{-1}$; 3344, 2920.

Elementary analysis data: caluculated value for $C_8H_{12}NO_2Cl$: C: 50.67%, H: 6.38%, N: 7.39%, Cl: 18.69%; analyzed value: C: 50.68%, H: 6.33%, N: 7.26%, Cl: 18.69%.

EXAMPLE 2

| Base composition: | Content (%) |
| --- | --- |
| oleic acid | 10 |
| diethanolamide oleate | 8 |
| oleyl alcohol | 2 |
| polyoxyethylene octyldodecyl ether (average addition of EO: 20 mol) | 10 |
| ethanol | 15 |
| propylene glycol | 10 |
| ammonium chloride | 3 |
| 25% ammonia | 7 |
| water | 35 |

To 100 g of a base consisting of the above composition were added 0.01 mol of each color-developing material and 0.01 mol of each coupling agent, as specified in Tables 1 and 2 below. Next, the pH value of the composition was adjusted to 9.5 with ammonia. Thus the dyeing composition of the present invention and comparative dyeing composition were produced.

100 g of the dyeing composition of the present invention was mixed with the same weight of a 6% aqueous solution of hydrogen peroxide to thereby give a dyeing solution. This dyeing solution was applied to human grizzled hair and allowed to stand at 30° C. for 30 minutes. Then the hair was washed with the use of a common shampoo and dried. The color tone of hair thus dyed was observed. Table 1 shows the results. The color tone, chroma, color intensity and dye stability for fading were also evaluated. Table 2 shows the results. Each dyeing composition showed excellent dyeing properties.

The dye stability for fading was evaluated by comparing each sample after storing at 40° C. under 70%RH for 100 hours with a comparative sample stored at −5° C. with the naked eye.

Color-developing Material $P_1$: p-aminophenol
$P_2$: 5-aminosalicylic acid
$P_3$: 2-chloro-4-aminophenol.
$P_4$: 2,2,2-trifluoromethyl-4-aminophenol.
$P_5$: p-phenylenediamine
$P_6$: toluene-2,5-diamine Coupling agent $C_2$: 2-methyl-5-aminophenol
$C_5$: 2-methyl-4-methoxy-5-aminophenol
$C_6$: 2-methyl-4-methoxy-5-aminophenol hydrochloride.

Criteria for evaluation:

A: very good.
B: average.
C: poor.

TABLE 1

| Product of the invention | Color-developing material | Coupling agent | Color tone |
| --- | --- | --- | --- |
| 1-1 | $P_5$ | $C_5$ | Reddish Purple |
| 1-2 | $P_6$ | $C_5$ | Reddish Purple |
| 1-3 | $P_1$ | $C_5$ | Red |
| 1-4 | $P_2$ | $C_5$ | Orange Red |
| 1-5 | $P_3$ | $C_5$ | Orange Yellow |
| 1-6 | $P_4$ | $C_5$ | Yellow |
| 1-7 | $P_1$ | $C_6$ | Red |

TABLE 2

| | Product of the Invention | | | Comparative Product | |
| --- | --- | --- | --- | --- | --- |
| | 1-3 | 1-4 | 1-7 | 1-1 | 1-2 |
| Color-developing material | $P_1$ | $P_2$ | $P_1$ | $P_1$ | $P_2$ |
| Coupling agent | $C_5$ | $C_5$ | $C_6$ | $C_2$ | $C_2$ |
| Dyed hair trace: | | | | | |
| Color tone | Red | Orange Red | Red | Red | Orange Red |
| Chroma | A | A | A | B | B |
| Color intensity | A | A | A | B | B |
| Dye stability for fading | A | A | A | B | B |

EXAMPLE 3

(i) To 13 ml of acetic anhydride were added 1.90 g (12.1 mmol) of 2-methyl-4-methoxy-5-aminophenol and 0.1 ml of concentrated sulfuric acid. The mixture was stirred at room temperature for 2 hours. After allowing to cool, 50 ml of (ice-)cold water was poured thereto and the mixture was allowed to stand overnight to thereby decompose the acetic anhydride. The crystals thus precipitated were filtered and recrystallized from benzene. Thus 1.85 g (7.8 mmol) of 2-methyl-4-methoxy-5-acetylaminophenyl acetate was obtained. The yield was 65%.

Physical Properties of 2-methyl-4-methoxy-5-acetylaminophenyl acetate m.p.: 150.5°–151.3° C.

1H-NMR spectra (200 MHz, DMSO-$d_6$): δppm; 2.06 (3H, s), 2.07 (3H, s), 2.27 (3H, s), 3.82 (3H, s), 6.92 (1H, s), 7.70 (1H, s)

IR spectra (KBr): $v cm^{-1}$; 3322, 2962, 2842, 1755, 1662.

Elementary analysis data: calculated value for $C_{12}H_{15}NO_4$: C: 60.96%, H: 6.39%, N: 5.92% analyzed value: C: 60.89%, H: 6.60%, N: 5.84%

(ii) To 35 ml of a 0.4N aqueous solution of sodium hydroxide were added 1.70 g (7.17 mmol) of 2-methyl-4-methoxy-5-acetylaminophenyl acetate and 10 ml of ethanol. The mixture was stirred at room temperature for 10 minutes. When crystals were completely dissolved, the stirring was ceased. Then 0.3 ml of acetic acid was added and thus crystals were precipitated. The crystals were collected by filtration, purified by column chromatography (Silica Gel 60, trade name, manufactured by Merck Co., 230–400 mesh, 200 g, eluent: ethyl acetate) and recrystallized from the solvent mixture of ethyl acetate/hexane (2:1). Thus 1.05 g (5.38 mmol) of 2-methyl-4-methoxy-5-acetylaminophenol was obtained. The yield was 75%.

Physical Properties of
2-methyl-4-methoxy-5-acetylaminophenol m.p.: 212.0°–215.4° C.

$^1$H-NMR spectra (200 MHz, DMSO-$d_6$): δppm; 2.17 (3H, s), 2.19 (3H, s), 3.84 (3H, s), 6.85 (1H, s), 7.67 (1H, s), 8.94 (1H, s), 9.04 (1H, brs).

IR spectra (KBr): νcm$^-$; 3390, 3136, 1653.

Elementary analysis data: calculated value for $C_{10}H_{13}NO_3$: C: 61.53%, H: 6.71%, N: 7.17%; analyzed value: C: 6.54%, H: 7.06%, N: 7.10%

EXAMPLE 4

(i) 20 ml of pyridine was cooled to 0° C. and 2.10 g (3.70 mmol) of 2-methyl-4-methoxy-5-aminophenol and 5.3 g (46.2 mmol) of methanesulfonyl chloride were added thereto. The mixture was adjusted to room temperature followed by stirring for 1 hour. Then 200 ml of water was poured thereto and the mixture was extracted with 300 ml of chloroform, and the extra was washed with 2N hydrochloric acid and a saturated aqueous solution of sodium hydrogencarbonate and dried over anhydrous Glauber's salt. After distilling off the solvent under reduced pressure, brown crystals were obtained. These crystals were purified by column chromatography (the same as the one used in Example 3) and recrystallized from the solvent mixture of ethyl acetate/hexane (2:1). Thus 2.01 g (6.50 mmol) of 2-methyl-4-methoxy-5-mesylaminophenyl mesylate was obtained. The yield was 47%.

Physical Properties of
2-methyl-4-methoxy-5-mesyl-aminophenyl mesylate m.p.: 114.5°–115.5° C.

$^1$H-NMR spectra (200 MHz, DMSO-$d_6$); δppm; 2.27 (3H, s), 2.94 (3H, s), 3.40 (3H, s), 3.89 (3H, s), 7.06 (1H, s), 7.22 (1H, s), 9.10 (1H, brs).

IR spectra (KBr): νcm$^{-1}$; 3248, 1354, 1332, 1174, 1154,

Elementary analysis data: calculated value for $C_{10}H_{15}NO_6S$: C: 38.83%, H: 4.89%, N: 4.53%, S: 20.73%; analyzed value: C: 38.77%, H: 5.24%, N: 4.50%, S: 20.77%.

(ii) To 50 ml of water were added 3.0 g of sodium hydroxide and 1.40 g (4.53 mmol) of 2-methyl-4-methoxy-5-mesylphenyl mesylate. The mixture was heated under reflux for 1 hour. After cooling, 10 ml of concentrated hydrochloric acid was added thereto and thus crystals were precipitated. These crystals were collected by filtration, washed with water and recrystallized from the solvent mixture of ethyl acetate/hexane (2:1). Thus 0.72 g (3.12 mmol) of 2-methyl-4-methoxy-5-mesylaminophenol was obtained. The yield was 69%.

Physical Properties of
2-methyl-4-methoxy-5-mesylaminophenol m.p.: 153.1°–154.3° C.

$^1$H-NMR spectra (200 MHz, DMSO-$d_6$); δppm; 2.09 (3H, s), 2.87 (3H, s), 3.72 (3H, s), 6.76 (1H, s), 6.80 (1H, s), 8.67 (1H, brs), 8.96 (1H, s).

IR spectra (KBr): νcm$^{-1}$: 3442, 3256, 1308, 1203, 1155.

Elementary analysis data: calculated value for $C_9H_{13}NO_4S$: C: 46.74%, H: 5.67%, N: 6.06%, S: 13.86%; analyzed value: C: 46.82%, H: 6.06%, N: 6.04%, S: 13.88%.

EXAMPLE 5

| Base composition: | Content (%) |
|---|---|
| oleic acid | 10 |
| diethanolamide oleate | 8 |
| oleyl alcohol | 2 |
| polyoxyethylene octyldodecyl ether (average addition of EO: 20 mol) | 10 |
| ethanol | 15 |
| propylene glycol | 10 |
| ammonium chloride | 3 |
| 25% ammonia | 7 |
| water | 35 |

To 100 g of a base consisting of the above composition, were added 0.01 mol of each color-developing material and 0.01 mol of each coupling agent, as specified in Table 3 or 4 below. Next, the pH value of the composition was adjusted to 9.5 with ammonia. Thus the dyeing composition of the present invention and the comparative dyeing composition were produced.

100 g of the dyeing composition of the present invention was mixed with the same weight of a 6% aqueous solution of hydrogen peroxide to thereby give a dyeing solution. This dyeing solution was applied to human grizzled hair and allowed to stand at 30° C. for 30 minutes. Then the hair was washed with the use of a common shampoo and dried. The color tone of hair thus dyed was observed. Table 3 shows the results. The color tone, chroma and dye stability for fading of the dye were also evaluated. Table 4 shows the results. Each dyeing composition showed excellent dyeing properties.

The dye stability for fading was evaluated by comparing each sample after storing at 40° C. under RH 70% for 100 hours with a comparative sample stored at −5° C. with the naked eye.

Color-developing Material $P_1$: p-aminophenol
$P_2$: 5-aminosalicylic acid.
$P_5$: p-phenylenediamine
$P_6$: toluene-2,5-diamine Coupling Agent $C_7$: 2-methyl-4-methoxy-5-acetylaminophenol
$C_8$: m-phenylenediamine
$C_{22}$: 2-methyl-4-methoxy-5-acetylaminophenyl acetate Criteria for Evaluation A: very good.
B: good.
C: somewhat poor.
D: poor.

TABLE 3

| Production of The Invention | Color-developing Material | Coupling agent | Color-tone |
|---|---|---|---|
| 2-1 | $P_5$ | $C_7$ | Blue |
| 2-2 | $P_6$ | $C_7$ | Violet Blue |
| 2-3 | $P_1$ | $C_7$ | Orange Yellow |
| 2-4 | $P_2$ | $C_7$ | Yellow |
| 2-5 | $P_5$ | $C_{22}$ | Blue |
| 2-6 | $P_6$ | $C_{22}$ | Violet Blue |

TABLE 4

|  | Product of the Invention | | | | | | Comparative product | |
| --- | --- | --- | --- | --- | --- | --- | --- | --- |
|  | 2-1 | 2-2 | 2-3 | 2-4 | 2-5 | 2-6 | 2-1 | 2-2 |
| Color-developing material | P$_5$ | P$_6$ | P$_1$ | P$_2$ | P$_5$ | P$_6$ | P$_5$ | P$_6$ |
| Coupling agent | C$_7$ | C$_7$ | C$_7$ | C$_7$ | C$_{22}$ | C$_{22}$ | C$_8$ | C$_8$ |
| Dyed hair trace: |  |  |  |  |  |  |  |  |
| Color tone | Blue | Violet Blue | Orange Yellow | Yellow | Blue | Violet Blue | Blue | Blue |
| Chroma | A | A | B | B | A | A | B | B |
| Dye stability for fading | A | A | A | A | A | A | D | D |

EXAMPLE 6

(i) To 20 ml of dioxane were added 5.10 g (33.3 mmol) of 2-methyl-4-methoxy-5-aminophenol and 1.86 g of calcium carbonate, and the temperature of the mixture was evaluated to 90° C. 3.90 ml (5.38 mmol) of β-chloroethyl chloroformate was added thereto and the resulting mixture was stirred at 90° C. for 1 hour. After cooled with ice, insoluble inorganic salts were filtered off and 150 ml of (ice-)cold water was poured into the filtrate. The crystals thus precipitated were filtered and washed with water. Thus, 5.80 g (22.3 mmol) of N-(2-methoxy-4-methyl-5-hydroxyphenyl)-β-chloroethyl carbamate was obtained. The yield was 67%.

Physical Properties of N-(2-methoxy-4-methyl-5-hydroxyphenyl)-β-chloroethyl carbamate m.p.: 177.0°–180.5° C.

$^1$H-NMR spectra (200 MHz, DMSO-d$_6$): δppm; 2.07 (3H, s), 3.69 (3H, s), 3.83 (2H, t, J=5.3 Hz), 4.30 (2H, t, J=5.3 Hz), 6.73 (1H, s), 7.16 (1H, s), 8.32 (1H, s), 8.85 (1H, s).

IR spectra (KBr): νcm$^{-1}$; 3408, 1694.

Elementary analysis data: caluculated value for C$_{11}$H$_{14}$NO$_4$Cl: C: 50.88%, H: 5.43%, N: 5.39%, Cl: 13.65%; analyzed value: C: 50.70%, H: 5.41%, N: 5.11%, Cl: 13.59%.

(ii) To 10 ml of water was added 1.87 g of sodium hydroxide, and the temperature of the solution was elevated to 45° C. 5.50 g (21.2 mmol) of N-(2-methoxy-4-methyl-5-hydroxyphenyl)-2-chloroethyl carbamate was added thereto and the resulting mixture was stirred at 45° C. for 15 minutes. After cooled with ice, 20 ml of (ice)-cold water was poured into the reaction mixture and concentrated hydrochloric acid was added thereto until no further crystals were precipitated. The crystals were collected by filtration, washed with water and recrystallized from ethanol. Thus 3.03 g (13.6 mmol) of N-(2-methoxy-4-methyl-5-hydroxyphenyl)-1,3-oxazolidin-2-one was obtained. The yield was 64%.

Physical Properties of N-(2-methoxy-4-methyl-5-hydroxy-phenyl)-1,3-oxazolidin-2-one m.p.: 193.5°–196.8° C.

$^1$H-NMR spectra (200 MHz, DMSO-d$_6$) δppm; 2.13 (3H, s), 3.71 (3H, s), 3.82 (2H, t, J=7.5 Hz), 4.39 (2H, t, J=7.5Hz), 6.71 (1H, s), 6.84 (1H, s), 9.03 (1H, s).

IR spectra: νcm$^{-1}$; 3256, 1714.

Elementary analysis data: caluculated value for C$_{11}$H$_{13}$NO$_4$: C: 59.19%, H: 5.87%, N: 6.27%; analyzed value: C: 59.28%, H: 5.94%, N: 6.22%.

(iii) 10 ml of 5N sodium hydroxide was heated to 70° C., and 2.76 g (12.4 mmol) of N-(2-methoxy-4-methyl-5-hydroxyphenyl)-1,3-oxazolidin-2-one was added thereto, and then the resulting mixture was stirred at 70° C. for 1 hour. After allowing to cool, 40 ml of water was poured into the reaction mixture, and acetic acid was added thereto until no further crystals were precipitated. The crystals were filtered, washed with water and recrystallized from the solvent mixture of water/ethanol (4:1, by volume). Thus, 1.10 g (5.6 mmol) of 2-methyl-4-methoxy-5-(β-hydroxyethylamino)phenol was obtained. The yield was 45%.

Physical Properties of 2-methyl-4-methoxy-5-(β-hydroxyethyl-amino)phenol m.p.: 81.5√–82.5° C.

$^1$H-NMR spectra (200 MHz, DMSO-d$_6$): δppm; 1.99 (3H, s), 2.99 (2H, t, d, J=5.5, 5.5Hz), 3.57 (2H, t, d, J=5.5, 5.5 Hz), 3.66 (3H, s), 4.51 (1H, brt, J=5.5 Hz), 4.78 (1H, t, J=5.5 Hz), 6.07 (1H, s), 6.52 (1H, s), 8.41 (1H, s).

IR-spectra (KBr): νcm$^{-1}$; 3440, 3345, 3240.

Elementary analysis data: caluculated value for C$_{10}$H$_{16}$NO$_3$Cl: C: 51.40%, H: 6.90%, N: 5.99%, Cl: 15.17%; analyzed value: C: 51.39%, H: 6.88%, N: 5.91%, Cl: 15.03%.

EXAMPLE 7

| Base composition: | Content (%) |
| --- | --- |
| oleic acid | 10 |
| diethanolamide oleate | 8 |
| oleyl alcohol | 2 |
| polyoxyethylene octyldodecyl ether (average addition of EO: 20 mol) | 10 |
| ethanol | 15 |
| propylene glycol | 10 |
| ammonium chloride | 3 |
| 25% ammonia | 7 |
| water | 35 |

To 100 g of a base consisting of the above composition were added 0.01 mol of each color-developing material and 0.01 mol of each coupling agent, as specified in Tables 5 and 6 below. Next, the pH value of the composition was adjusted to 9.5 with ammonia. Thus the dyeing compositions of the present invention and comparative dyeing compositions were produced.

100 g of the dyeing composition of the present invention was mixed with the same weight of a 6% aqueous solution of hydrogen peroxide to thereby give a dyeing solution. This dyeing solution was applied to human grizzled hair and allowed to stand at 30° C. for 30 minutes. Then the hair was washed with the use of a common shampoo and dried. The color tone of hair thus dyed was observed. Table 5 shows the results. The color tone, chroma, color intensity and dye stability for fading of the dye were also evaluated. Table 6 shows the results. Each dyeing composition showed excellent dyeing properties.

The dye stability for fading was evaluated by comparing each sample after storing at 40° C. under 70%RH for 100 hours with a comparative sample stored at −5° C. with the naked eye.

Color-developing Material $P_1$: p-aminophenol
$P_2$: 5-aminosalicylic acid
$P_3$: 2-chloro-4-aminophenol.
$P_4$: 2,2,2-trifluoromethyl-4-aminophenol.
$P_5$: p-phenylenediamine
$P_6$: toluene-2,5-diamine Coupling Agent $C_1$: 2-methyl-4-methoxy-5-(2-hydroxyethyl)aminophenol
$C_2$: 2-methyl-5-aminophenol
$C_3$: 2-methyl-5-(2-hydroxyethyl)aminophenol
$C_4$: 2-methyl-4-methoxy-5-(2-hydroxyethyl)aminophenol hydrochloride.

Criteria for Evaluation

A: very good.
B: average.
C: poor.

TABLE 5

| Product of the invention | Color-developing material | Coupling agent | Color tone |
| --- | --- | --- | --- |
| 3-1 | $P_1$ | $C_1$ | Red |
| 3-2 | $P_2$ | $C_1$ | Orange Red |
| 3-3 | $P_3$ | $C_1$ | Orange Red |
| 3-4 | $P_4$ | $C_1$ | Yellow |
| 3-5 | $P_5$ | $C_1$ | Reddish Purple |
| 3-6 | $P_6$ | $C_1$ | Reddish Purple |

TABLE 6

| | Product of the Invention | | | Comparative product | | | |
| --- | --- | --- | --- | --- | --- | --- | --- |
| | 3-1 | 3-2 | 3-3 | 3-1 | 3-2 | 3-3 | 3-4 |
| Color-developing material | $P_1$ | $P_2$ | $P_1$ | $P_1$ | $P_2$ | $P_1$ | $P_2$ |
| Coupling agent | $C_1$ | $C_1$ | $C_4$ | $C_2$ | $C_2$ | $C_3$ | $C_3$ |
| Dyed hair trace: | | | | | | | |
| Color tone | Red | Orange Red | Red | Red | Orange Red | Red | Orange Red |
| Chroma | A | A | A | B | B | B | B |
| Color intensity | A | A | A | B | B | B | B |
| Dye stability for fading | A | A | A | B | B | A | A |

EXAMPLE 8

(i) 1.55 g of 10% palladium-on-carbon, 18.8 g (71.9 mmol) of 2-methyl-4-methoxy-5-nitrophenyl mesylate and 120 ml of ethanol were fed into an autoclave (200 ml), and the mixture was then hydrogenated at 50° C. under 50 g/cm² for 1 hours with stirring. After allowing to cool, palladium-on-carbon was filtered off and the solvent was distilled off under reduced pressure to obtain brown crystals. The crystals thus obtained were recrystallized from ethanol to thereby give 13.4 g (58.2 mmol) of 2-methyl-4-methoxy-5-aminophenyl mesylate in the form of yellow needle-like crystals. The yield was 81%.

Physical Properties of
2-methyl-4-methoxy-5-aminophenyl mesylate m.p.: 87.0°–88.0° C.
$^1$H-NMR spectra (200 MHz, $CDCl_3$): δppm; 2.24 (3H, s), 3.13 (3H, s), 3.83 (3H, s), 6.79 (1H, s), 6.85 (1H, s).
IR spectra (KBr): νcm$^{-1}$; 3464, 3380, 1518, 1352.
Elementary analysis data: calculated value for $C_9H_{13}NO_4S$: C: 46.74%, H: 5.67%, N: 6.06%, S: 13.86%. analyzed value: C: 46.74%, H: 5.67%, N: 5.85%, S: 13.80%.

(ii) 7.52 g (32.6 mmol) of 2-methyl-4-methoxy-5-aminophenyl mesylate, 90 ml of ethanol and 4.2 ml (3.5 g, 60 mmol) of propylene oxide were fed into an autoclave (200 ml) and the mixture was stirred at 70° C. for 35 hours. After allowing to cool, the solvent was distilled off under reduced pressure to obtain a brown oily matter. The oily matter thus obtained was subjected to silica gel chromatography (Silica Gel 60, trade name, manufactured by Merck Co., 70–230 mesh, 300 g, eluent: chloroform/ethyl acetate (1:1 by volume)), and thereby give 0.33 g (1.4 mmol, 6%) of the starting material from the first fraction, 6.46 g (22.4 mmol, 69%) of 2-methyl-4-methoxy-5-(2-hydroxypropyl)aminophenyl mesylate from the second fraction in the form of an oily matter and 1.81 g (5.2 mmol, 16%) of 2-methyl-4-methoxy-5-bis(2-hydroxypropyl)aminophenyl mesylate from the third fraction in the form of brown crystals.

Physical Properties of
2-methyl-4-methoxy-5-(2-hydroxypropyl) aminophenyl mesylate Form: pale yellow oil
$^1$H-NMR spectra (200 MHz, DMSO-$d_6$): δppm; 1.11 (3H, d, J=6.8 Hz), 2.15 (3H, s), 2.83 (1H, m), 3.01 (1H, m), 3.34 (3H, s), 3.79 (3H, s), 3.82 (1H, m), 4.5 (br), 6.45 (1H, s), 6.73 (1H, s).
IR spectra (KBr): νcm$^{-1}$; 3450, 1532, 1362.
Elementary analysis data: calculated value for $C_{12}H_{19}NO_5S$: C: 49.81%, H: 6.62%, N: 4.84%, S: 11.08%. analyzed value: C: 49.52%, H: 6.85%, N: 5.02%, S: 10.88%.

Physical Properties of
2-methyl-4-methoxy-5-bis(2-hydroxy-propyl)aminophenyl mesylate m.p.: 128.0°–129.0° C.
$^1$H-NMR spectra (200 MHz, $CDCl_3$): δppm; 1.09 (6H, s, J=6.2 Hz), 2.34 (3H, s), 2.8 (2H, m), 3.1 (2H, s), 3.17 (3H, s), 3.50 (2H, br), 3.61 (2H, m), 3.88 (3H, s), 6.78 (1H, s), 7.16 (1H, s).

IR spectra (KBr): $\nu cm^{-1}$; 3272, 1514, 1364.

Elementary analysis data: calculated value for $C_{15}H_{25}NO_6S$: C: 51.86%, H: 7.25%, N: 4.03%, S: 9.23%. analyzed value: C: 51.78%, H: 7.21%, N: 3.78%, S: 9.35%.

(iii) Into 100 ml of methanol was added 2.0 g (13.1 mmol) of 2-methyl-4-methoxy-5-(2-hydroxypropyl)aminophenyl mesylate. After conducting nitrogen substitution at room temperature, 40 ml of 7.5N aqueous solution of sodium hydroxide was added to the mixture and the resulting mixture was heated under reflux for 7 hours with blowing nitrogen gas thereinto. After allowing to cool, the mixture was neutralized with acetic acid and poured into 400 ml of water. The resulting solution was extracted with 400 ml of ethyl acetate. The organic layer was washed with a saturated aqueous solution of common salt and dried over anhydrous sodium sulfate. The solvent was distilled off under reduced pressure to obtain an oily matter. The oily matter was crystallized from the solvent mixture of hexane/ethyl acetate (1:1 by volume) to give 2.30 g (10.9 mmol) of 2-methyl-4-methoxy-5-(2-hydroxypropyl)aminophenol. The yield was 49%.

Physical Properties of 2-methyl-4-methoxy-5-(2-hydroxypropyl) aminophenol 124.5°–126.0° C.

$^1$H-NMR spectra (200 MHz, DMSO-d$_6$): $\delta$ppm; 1.26 (3H, d,J=6.7 Hz), 2.17 (3H, d,J=6.7 Hz), 2.99 (1H, dd,J=13.4, 7.3 Hz), 3.18 (1H, dd,J=13.4, 4.6 Hz), 3.80 (3H, s), 4.04 (1H, m), 4.5 (br), 6.21 (1H, s), 6.54 (1H, s).

IR spectra (KBr): $\nu cm^{-1}$; 3420, 3384, 3340 (sh.)

Elementary analysis data: calculated value for $C_{11}H_{17}NO_3$: C: 62.54%, H: 8.11%, N: 6.63%; analyzed value: C: 62.45%, H: 8.11%, N: 6.56%.

EXAMPLE 9

Into 15 ml of benzene were added 2.10 g (13.7 mmol) of 2-methyl-4-methoxy-5-aminophenol, 1.28 g (13.9 mmol, 1.0 eq.) of methyl fluoroacetate and 1.64 g (30.4 mmol) of sodium methoxide and the mixture was heated under reflux for 6.5 hours. After allowing to cool, the mixture was poured into 300 ml of water, and neutralized with acetic acid and extracted with 200 ml of ethyl acetate. The organic layer was washed with a saturated aqueous solution of common salt and dried over anhydrous sodium sulfate. The solvent was distilled off under reduced pressure to obtain dark-brown crystals. The crystals were purified by silica gel column chromatography (Silica Gel 60, trade name, manufactured by Merck Co., 70–230 mesh, 200 g, eluent: ethyl acetate) and pale brown solid matters were obtained from the 600–900 ml fraction. The solid matters were recrystalized from the solvent mixture of hexane/ethyl acetate (2:1 by volume) to give 230 mg (1.9 mmol) of 2-methyl-4-methoxy-5-fluoroacetylaminophenol. The yield was 8%.

Physical Properties of 2-methyl-4-methoxy-5-fluoroacetylaminophenol.

m.p.: 171.5°–173.0° C.

$^1$H-NMR spectra (200 MHz, DMSO-d$_6$): $\delta$ppm; 2.08 (3H, 2), 3.75 (3H, s), 4.99 (2H, d, J=46.7Hz), 6.80 (1H, s), 7.60 (1H, s), 8.88 (1H, brs), 8.95 (1H, s).

(KBr): $\nu cm^{-1}$; 3428, 3224, 1676.

IR spectra (KBr): $\nu cm^{-1}$; 3428, 2334, 1676.

Elementary analysis data: calculated value for $C_{10}H_{12}NO_3F$: C: 56.33%, H: 5.67%, N: 6.57%; analyzed value: C: 56.08%, H: 5.88%, N: 6.50%.

EXAMPLE 10

2.08 g (11.0 mmol) of 2-methyl-4-methoxy-5-aminophenol was added to 200 ml of pyridine and the mixture was cooled to 0° C. 4.20 g (24.1 mmol, 2.2 eq.) of difluoroacetic anhydride was added to the mixture and the mixture was stirred at room temperature for 30 minutes. The mixture was poured into 200 ml of water and the mixture was extracted with 200 ml of chloroform. The organic layer was washed with a saturated aqueous solution of common salt and dried over anhydrous sodium sulfate. The solvent was distilled off under reduced pressure to obtain crystals. The crystals were added to 35 ml of 0.4N aqueous solution of sodium hydroxide and 10 ml of ethanol was added thereto, followed by stirring at room temperature for 15 minutes. The solution was neutralized with acetic acid and the crystals thus precipitated were filtered out. The crystals were recrystallized from the solvent mixture of hexane/ethyl acetate (2:1 by volume) to give 1.30 g (5.6 mmol) of 2-methyl-4-methoxy-5-difluoroacetylaminophenol in the form of colorless crystals. The yield was 52%.

Physical Properties of 2-methyl-4-methoxy-5-difluoroacetyl-aminophenol 202.0°–204.0° C.

$^1$H-NMR spectra (200 MHz, DMSO-d$_6$) $\delta$ppm; 2.10 (3H, s), 3.75 (3H, s), 6.46 (1H, t, J=52.9 Hz), 6.82 (1H, s), 7.44 (1H, s), 9.00 (1H, s), 9.75 (1H, brs).

IR spectra (KBr): $\nu cm^{-1}$; 3408, 3304, 1694.

Elementary analysis data: calculated value for $C_{10}H_{11}NO_3F_2$: C: 51.95%, H: 4.80%, N:6.06%, analyzed value: C: 52.11%, H: 4.85%, N: 6.08%.

EXAMPLE 11

2.0 g (13.1 mmol) of 2-methyl-4-methoxy-5-aminophenol was added to 20 ml of pyridine and the mixture was cooled to 0° C. 3.0 ml (4.5 g, 21 mmol) of trifluoroacetic anhydride was added to the mixture and stirred at room temperature for 2 hours. The mixture was poured into 200 ml of water and the mixture was extracted with 300 ml of chloroform. The organic layer was washed with a saturated aqueous solution of common salt and dried over anhydrous sodium sulfate. The solvent was distilled off under reduced pressure to obtain dark-brown solid matter. The solid matter was purified by silica gel column chromatography (Silica Gel 60, trade name, manufactured by Merck Co., 70–230 mesh, 100 g, eluent: ethyl acetate) and thereby colorless crystals were obtained from the 200 –500 ml fraction. The crystals were recrystallized from the solvent mixture of hexane/ethyl acetate (2:1 by volume) to give 280 mg (1.1 mol) of 2-methyl-4-methoxy-5-trifluoroacetylaminophenol in the form of colorless crystals. The yield was 9%.

Physical Properties of 2-methyl-4-methoxy-5-trifluoroacetylaminophenol m.p. 201.5°–203.0° C.

$^1$H-NMR spectra (200 MHz, DMSO-d$_6$): $\delta$ppm; 2.12 (3H, s), 3.74 (3H, s), 6.89 (1H, s), 6.92 (1H, s), 9.08 (1H, s), 10.45 (1H, s).

IR spectra (KBr): $\nu cm^{-1}$; 3400, 1713.

Elementary analysis data: calculated value for $C_{10}H_{10}NO_3F_3$: C: 48.26%, H: 4.04%, N: 5.62%; analyzed value: C: 48.50%, H: 4.19%, N: 5.57%.

EXAMPLE 12

(i) 2 g (10.6 mmol) of 2-methyl-4-methoxy-5-aminophenol and 4.9 g (21.7 mmol) of benzoic anhydride were dissolved into 200 ml of pyridine and the solution was stirred at room temperature overnight. The solution was poured over ice, and solid matters thus precipitated were collected by filtration followed by washed with water and recrystallized from the solvent mixture of benzene/hexane to give 3.10 g (8.6 mmol) of 2-methyl-4-methoxy-5-benzoylaminophenyl benzoate in the form of pale brown crystals. The yield was 81%.

Physical Properties of
2-methyl-4-methoxy-5-benzoylaminophenyl benzoate m.p.: 203.5°–207.8° C.
$^1$H-NMR spectra (200 MHz, CDCl$_3$); δppm; 8.53 (broad s, 1H, NHB$_2$), 8.41 (s, 1H, arm-H), 8.37 (dd, J$_1$=1.3Hz, J$_2$=8.3Hz, 2H, arm-H), 8.03 (dd, J$_1$=1.8Hz, J$_2$=7.6Hz, 2H, arm-H), 7.4–7.7 (m, 6H, arm-H), 6.81 (s, 1H, arm-H), 3.95 (s, 3H, CH$_3$O), 2.22 (s, 2H, CH$_3$).
IR spectra (KBr): νcm$^{-1}$; 1654, 1722.
Elementary analysis data: caluculated value for $C_{22}H_{19}NO_4$: C: 73.12%, H: 5.30%, N: 3.88%; analyzed value: C: 73.00%, H: 5.52%, N: 4.16%.

(ii) 3 g (8.3 mmol) of 2-methyl-4-methoxy-5-benzoylaminophenyl benzoate was added into the mixture of 50 ml of sodium hydroxide and 50 ml of ethanol and the solution was heated at 100° C. under reflux for 2.5 hours. 40 ml of 1N hydrochloric acid was added to the reaction mixture and precipitates were filtered, washed with water and recrystallized from ethanol to give 1.2 g (4.6 mmol) of 2-methyl-4-methoxy-5-benzoylaminophenol in the form of pale yellow plate-like crystals. The yield was 78%.

Physical Properties of
2-methyl-4-methoxy-5-benzoylaminophenol m.p.: 193.1°–193.4° C.
$^1$H-NMR spectra (200 MHz, CDCl$_3$); δppm; 8.60 (broad s, 1H, NHB$_2$), 8.42 (s, 1H, arm-H), 7.92–7.88 (m, 2H, arm-H), 7.46–7.64 (broad d, 4H, arm-H, OH), 6.70 (s, 1H, arm-H), 3.88 (s, 3H, CH$_3$O), 2.25 (s, 3H, CH$_3$).
IR spectra (KBr): νcm$^-$; 3244, 1644.
Elementary analysis data: caluculated value for $C_{15}H_{15}NO_3$: C: 70.02%, H: 5.88%, N: 5.44%; analyzed value: C: 70.17%, H: 6.03%, N: 5.44%.

EXAMPLE 13

5.0 g (32.7 mmol) of 2-methyl-4-methoxy-5-aminophenol, 500 ml of palladium-on-carbon, 100 ml of methanol and 1.72 g of acetaldehyde were fed into an autoclave (200 ml). The mixture was then hydrogenated at 50° C. under 50 kg/cm$^2$ for 6 hours. After allowing to cool, the palladium-on-carbon was filtered off and the solvent was distilled off under reduced pressure to obtain brown crystals. The crystals were separated and purified by silica gel column chromatography (Silica Gel 60, trade name, manufactured by Merck Co., 230–400 mesh, 300 g, eluent: ethyl acetate/hexane (1:1 by volume)) to give 2.62 g (14.5 mmol) of 2-methyl-4-methoxy-5-ethylaminophenol from the first fraction in the form of pale red crystals and 1.86 g (8.90 mmol) of 2-methyl-4-methoxy-5-diethylaminophenol from the second fraction in the form of pale yellow crystals. The yields were 44% and 27%, respectively. Each of 2-methyl-4-methoxy-5-ethylaminophenol and 2-methyl-4-methoxy-5-diethylaminophenol was purified by recrystallization from the solvent mixture of ethyl acetate/hexane (1:2 by volume).

Physical Properties of
2-methyl-4-methoxy-5-ethylaminophenol m.p.: 110.2°–110.9C.
$^1$H-NMR spectra (200 MHz, DMSO-d$_6$); δppm; 1.14 (3H, t, J=7.2Hz), 1.98 (1H, s), 2.47 (2H, dq, J=7.2, 7.2 Hz), 3.65 (3H, s), 4.34 (1H, brt, J=7.2Hz), 6.05 (1H, s), 6.48 (1H, s), 8.38 (1H, s).
IR spectra (KBr): νcm$^{-1}$; 3324, 3132, 1204.
Elementary analysis data: calculated value for $C_{10}H_{15}NO_2$: C: 66.27%, H: 8,34%, N: 7.73%; analyzed value: C: 66.48%, H: 8.39%, N: 7.71%.

Physical Properties of
2-methyl-4-methoxy-5-diethylaminophenol m.p.: 94.0°–95.0C.
$^1$H-NMR spectra (200 MHz, DMSO-d$_6$); δppm; 0.92 (6H, t, J=7.2Hz), 2.04 (3H, s), 3.00 (4H, q, J=7.2Hz), 3.66 (3H, s), 6.38 (1H, s), 6.60 (1H, s), 8.52 (1H, s).
IR spectra (KBr): νcm$^{-1}$; 3180, 2976, 1208.
Elementary analysis data: calculated value for $C_{12}H_{19}NO_2$: C: 68.87%, H: 9.15%, N: 6.69%; analyzed value: C: 68.90%, H: 9.11%, N: 6.61%.

EXAMPLE 14

5.0 g (32.7 mmol) of 2-methyl-4-methoxy-5-aminophenol, 500 ml of palladium-on-carbon, 100 ml of methanol and 3.36 g of 35% formalin were fed into an autoclave (200 ml). The mixture was then hydrogenated at 50° C. under 50 kg/cm$^2$ for 6 hours. After allowing to cool, the palladium-on-carbon was filtered off and the solvent was distilled off to obtain brown crystals. The crystals were separated and purified by silica gel column chromatography (Silica Gel 60, trade name, manufactured by Merck Co., 230– 400 mesh, eluent: ethyl acetate/hexane (1:1 by volume)) to thereby give 2.45 g (14.7 mmol) of 2-methyl-4-methoxy-5-methylaminophenol from the first fraction in the form of pale brown crystals and 1.82 g (10.1 mmol) of 2-methyl-4-methoxy-5-dimethylaminophenol from the second fraction in the form of brown crystals. The yields were 45% and 31%, respectively. Then, 2-methyl-4-methoxy-5-methylaminophenol was dissolved into 50 ml of ethanol and a hydrogen chloride gas was blown thereto followed by addition of acetonitrile to thereby give 2-methyl-4-methoxy-5-methyl-aminophenol hydrochloride as the purified crystals. While 2-methyl-4-methoxy-5-dimethylaminophenol was recrystallized from the solvent mixture of ethyl acetate/hexane (1:2 by volume).

Physical Properties of
2-methyl-4-methoxy-5-methylaminophenol
hydrochloride m.p.: 230.5°–233.0° C.
$^1$H-NMR spectra (200 MHz, DMSO-d$_6$); δppm; 2.13 (3H, s), 2.76 (3H, s), 3.79 (3H, s), 6.96 (1H, s), 7.01 (1H, s).
IR spectra (KBr): νcm$^{-1}$; 3620, 3210, 2660, 2452, 1208.
Elementary analysis data: calculated value for $C_9H_{14}NO_2Cl$: C: 53.08%, H: 6.93%, N: 6.88%, Cl:

17.41%; analyzed value: C: 52.84%, H: 6.98%, N: 7.05%, Cl: 17.27%.

Physical Properties of 2-methyl-4-methoxy-5-dimethylaminophenol m.p.: 109.5°–110.5° C.

$^1$H-NMR spectra (200 MHz, DMSO-$d_6$); δppm; 2.04 (3H, s), 2.60 (6H, s), 3.66 (3H, s), 6.34 (1H, s), 6.58 (1H, s), 8.55 (1H, s).

IR spectra (KBr): $\nu cm^{-1}$; 3150, 2960, 1202.

Elementary analysis data: calculated value for $C_{10}H_{15}NO_2$: C: 66.27%, H: 8.34%, N: 7.73%. analyzed value: C: 66.42%, H: 8.25%, N: 7.85%.

EXAMPLE 15

The dyeing compositions of the present invention and the comparative dyeing compositions were produced in accordance with the manner as in Example 2 except that the color-developing material and the coupling agent each specified in table 7 or 8 below were used.

The dyeing solution was produced in the manner as in Example 2. This dyeing solution was applied to human grizzled hair and allowed to stand at 30° C. for 30 minutes. Then the hair was washed with the used of a common shampoo and dried. The color tone of the hair thus dyed was observed. Table 7 shows the results. The color tone, chroma, color intensity, and dye stability for fading were also evaluated. Table 8 shows the results. Each dyeing composition showed excellent dyeing properties.

The dye stability for fading was evaluated by comparing each sample after storing at 40° C. under 70%RH for 100 hours with ac comparative sample stored at −5° C. with the naked eye.

Color-developing Material $P_1$: p-aminophenol  
$P_2$: 5-aminosalicylic acid  
$P_3$: 2-chloro-4-aminophenol  
$P_4$: 2,2,2-trifluoromethyl-4-aminophenol  
$P_5$: p-phenylenediamine  
$P_6$: toluene-2, 5-diamine

Coupling Agent $C_9$: 2-methyl-4-methoxy-5-methylaminophenol  
$C_{10}$: 2-methyl-4-methoxy-5-dimethylaminophenol  
$C_{11}$: 2-methyl-4-methoxy-5-ethylaminophenol  
$C_{12}$: 2-methyl-4-methoxy-5-diethylaminophenol  
$C_{13}$: 2-methyl-4-methoxy-5-(2-hydroxypropyl)-aminophenol  
$C_{17}$: 2-methyl-4-methoxy-5-mesylaminophenol  
$C_{18}$: 2-methyl-4-methoxy-5-benzoylaminophenol  
$C_{19}$: 2-methyl-4-methoxy-5-fluoroacetylaminophenol  
$C_{20}$: 2-methyl-4-methoxy-5-difluoroacetylaminophenol  
$C_{21}$: 2-methyl-4-methoxy-5-trifluoroacetylaminophenol

Criteria for Evaluation

A: Very good.  
B: average.  
C: poor.

TABLE 7

| Product of the invention | Color-developing material | Coupling agent | Color tone |
| --- | --- | --- | --- |
| 4-1 | $P_1$ | $C_9$ | Red |
| 4-2 | $P_5$ | $C_9$ | Reddish Purple |

TABLE 7-continued

| Product of the invention | Color-developing material | Coupling agent | Color tone |
| --- | --- | --- | --- |
| 4-3 | $P_6$ | $C_9$ | Reddish Purple |
| 4-4 | $P_1$ | $C_{10}$ | Pink |
| 4-5 | $P_5$ | $C_{10}$ | Reddish Purple |
| 4-6 | $P_6$ | $C_{10}$ | Reddish Purple |
| 4-7 | $P_1$ | $C_{11}$ | Red |
| 4-8 | $P_5$ | $C_{11}$ | Reddish Purple |
| 4-9 | $P_6$ | $C_{11}$ | Reddish Purple |
| 4-10 | $P_1$ | $C_{12}$ | Pink |
| 4-11 | $P_5$ | $C_{12}$ | Reddish Purple |
| 4-12 | $P_6$ | $C_{12}$ | Reddish Purple |
| 4-13 | $P_1$ | $C_{13}$ | Red |
| 4-14 | $P_2$ | $C_{13}$ | Orange Red |
| 4-15 | $P_3$ | $C_{13}$ | Orange Yellow |
| 4-16 | $P_4$ | $C_{13}$ | Yellow |
| 4-17 | $P_5$ | $C_{13}$ | Reddish Purple |
| 4-18 | $P_6$ | $C_{13}$ | Reddish Purple |
| 4-19 | $P_6$ | $C_{17}$ | Yellow |
| 4-20 | $P_6$ | $C_{18}$ | Yellow |
| 4-21 | $P_5$ | $C_{19}$ | Blue |
| 4-22 | $P_6$ | $C_{19}$ | Blue |
| 4-23 | $P_5$ | $C_{20}$ | Purple |
| 4-24 | $P_6$ | $C_{20}$ | Purple |
| 4-25 | $P_1$ | $C_{20}$ | Reddish Purple |
| 4-26 | $P_5$ | $C_{21}$ | Reddish Purple |
| 4-27 | $P_6$ | $C_{21}$ | Reddish Purple |
| 4-28 | $P_1$ | $C_{21}$ | Red |

TABLE 8

| | Product of the Invention | | | |
| --- | --- | --- | --- | --- |
| | 4-1 | 4-7 | 4-13 | 4-14 |
| Color-developing material | $P_1$ | $P_1$ | $P_1$ | $P_2$ |
| Coupling agent | $C_9$ | $C_{11}$ | $C_{13}$ | $C_{13}$ |
| Dyed hair trace: | | | | |
| Color tone | Red | Red | Red | Orange Red |
| Chroma | B | B | B | B |
| Color intensity | B | B | A | A |
| Dye stability for fading | A | A | A | A |

While the invention has been described in detail and with reference to specific examples thereof, it will be apparent to one skilled in the art that various changes and modifications can be made therein without departing from the spirit and scope thereof.

What is claimed is:

1. A dyeing composition for keratin fibers comprising a color-developing material and a 2-alkyl-4-methoxy-5-substituted aminophenol derivative represented by formula (IV):

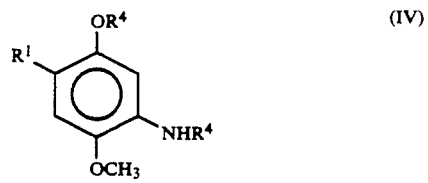

wherein $R^1$ represents a substituted or unsubstituted lower alkyl group; and $R^4$ and $R^{4'}$, which may be the same or different, each represents a substituted or unsubstituted lower alkyl group, a substituted or unsubstituted mono- or di-hydroxyalkyl group, a substituted or unsubstituted lower alkanoyl group, a substituted or unsubstituted arylcarbonyl group, or a substituted or unsubstituted lower alkylsulfonyl group.

2. A dyeing composition for keratin fibers as claimed in claim 1, wherein said color-developing material is the compound represented by formula (X):

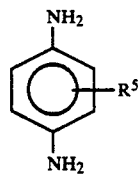

wherein $R^5$ represents a hydrogen atom, a chlorine atom, a methyl group, a hydroxyethyl group or a β-hydroxyethoxy group.

3. A dyeing composition for keratin fibers as claimed in claim 1, wherein both $R^4$ and $R^{4'}$ in formula (IV) represent an acetyl group.

* * * * *